US012806232B2

(12) United States Patent
Togashi et al.

(10) Patent No.: US 12,806,232 B2
(45) Date of Patent: Nov. 24, 2026

(54) SPECIFIC MARKER FOR IDENTIFYING T CELLS SPECIFICALLY ATTACKING CANCER CELLS

(71) Applicants: National Cancer Center, Tokyo (JP); Kotai Biotechnologies, Inc., Osaka (JP)

(72) Inventors: Yosuke Togashi, Tokyo (JP); Hiroyoshi Nishikawa, Tokyo (JP); Kazuo Yamashita, Osaka (JP); Nicolas Claude Paul Sax, Osaka (JP)

(73) Assignees: Kotai Biotechnologies, Inc., Osaka (JP); National Cancer Center, Tokyo (JP)

( * ) Notice: Subject to any disclaimer, the term of this patent is extended or adjusted under 35 U.S.C. 154(b) by 968 days.

(21) Appl. No.: 17/625,442

(22) PCT Filed: Jul. 9, 2020

(86) PCT No.: PCT/JP2020/026897
§ 371 (c)(1),
(2) Date: Jan. 7, 2022

(87) PCT Pub. No.: WO2021/006316
PCT Pub. Date: Jan. 14, 2021

(65) Prior Publication Data

US 2022/0257656 A1 Aug. 18, 2022

(30) Foreign Application Priority Data

Jul. 10, 2019 (JP) ................................ 2019-128517

(51) Int. Cl.

| | |
|---|---|
| ***A61P 43/00*** | (2006.01) |
| ***A61K 35/545*** | (2015.01) |
| ***A61K 40/11*** | (2025.01) |
| ***A61K 40/42*** | (2025.01) |
| ***C07K 14/005*** | (2006.01) |
| ***C12N 5/0783*** | (2010.01) |
| ***C12N 15/86*** | (2006.01) |

(52) U.S. Cl.
CPC ............ *A61K 35/545* (2013.01); *A61K 40/11* (2025.01); *A61K 40/4254* (2025.01); *C12N 5/0636* (2013.01); *C12N 5/0638* (2013.01)

(58) Field of Classification Search
None
See application file for complete search history.

(56) References Cited

FOREIGN PATENT DOCUMENTS

| | | | | |
|---|---|---|---|---|
| EP | 2203746 B1 * | 3/2013 | .......... G01N 33/505 |
| JP | 2018-533364 A | 11/2018 | |
| WO | WO-2017075389 A1 * | 5/2017 | ............ A61K 35/17 |
| WO | WO-2018182817 A1 * | 10/2018 | .......... A01N 1/0284 |

OTHER PUBLICATIONS

International Search Report, PCT/JP2020/026897, Japan Patent Office, Aug. 25, 2020.

* cited by examiner

*Primary Examiner* — Anna Skibinsky
*Assistant Examiner* — Catherine L McCormick
(74) *Attorney, Agent, or Firm* — Gavrilovich, Dodd & Lindsey LLP

(57) ABSTRACT

The present disclosure provides a specific marker for identifying T cells specifically attacking cancer cells and the utilization of the marker. According to the present disclosure, a marker that has a high specificity for identifying T cells specifically attacking cancer cells is provided. According to the present disclosure, treatment or prevention of cancer in a subject with the use of a cell subpopulation contained in a tumor tissue infiltrating $CD106^+$ T cell population or cells expressing a T cell receptor (TCR) expressed thereby can be provided. According to another embodiment of the present disclosure, a method for producing a cellular medicine can be provided. According to the present disclosure, further, a method that comprises using the amount of a cell subpopulation as an index of the responsiveness of a subject to a cancer immunotherapy can be provided. According to the present disclosure, furthermore, a method for acquiring a tumor specific TCR sequence can be provided.

5 Claims, 2 Drawing Sheets

Specificity to Tumor Cytotoxic T Cells of CD106

CD106 can select tumor cytotoxic T cells more specifically than other surface markers reported.

SPECIFIC MARKER FOR IDENTIFYING T CELLS SPECIFICALLY ATTACKING CANCER CELLS

CROSS REFERENCE TO RELATED APPLICATIONS

This application is a U.S. National Phase Application filed under 35 U.S.C. § 371 and claims priority to International Application No. PCT/JP2020/026897, filed Jul. 9, 2020, which application claims priority to Japanese Application No. 2019-128517, filed Jul. 10, 2019, the disclosures of which are incorporated herein by reference.

TECHNICAL FIELD

The present disclosure relates to medical or pharmaceutical field. More specifically, it relates to a technique for identifying T cells that specifically attack cancer cells, and can relate to cancer treatment. For example, the present disclosure can relate to adoptive cellular therapy or a method for producing the cells therefor, prediction of effect of cancer immunotherapy, and acquisition of a tumor-specific sequence, etc.

BACKGROUND TECHNOLOGY

Cancer immunotherapy has been focused as cancer treatment. In particular, the immune checkpoint inhibitor, for example, nivolumab, which is an anti-PD-1 antibody, shows a result in case of non-small cell lung cancer that largely exceeds docetaxel which was conventionally standard treatment in the full survival period, and is a standard treatment. It is considered that immune cells such as T lymphocytes are infiltrated into cancer tissue and related to defense reactions against cancer cells. However, it is known that not all of the infiltrating immune cells attack cancer cells. Introduction of the immune cells capable of attacking tumors (adoptive immunotherapy) is being studied as a cancer treatment.

SUMMARY OF THE INVENTION

Means for Solving the Problems

The inventors have found that CD106-positive tumor infiltrating T cells specifically attack cancer cells in local tumor, and CD106 can be used for identifying the T cells attacking cancer cells as a marker having high specificity. An embodiment of the present disclosure can relate to the treatment or prevention of cancer in a subject using cell subpopulations contained in tumor tissue infiltrating $CD106^+$ T cell populations. An embodiment of the present disclosure can relate to the treatment or prevention of cancer in a subject using T cell receptors (TCRs) expressed by cell subpopulations contained in tumor tissue infiltrating $CD106^+$ T cell populations or cells expressing the TCRs having the same antigen specificity as them. A further embodiment of the present disclosure can relate to a method for producing acellular medicine, comprising a step of purifying $CD106^+$ T cell populations from T cell populations. In the present disclosure, a method of using the amount of cell subpopulations contained in the $CD106^+$ T cell population of a subject as an index of responsiveness to cancer immunotherapy for the subject can also be provided. In the present disclosure, a method of acquiring the sequence of tumor-specific TCR can also be provided.

For example, in preferred embodiments of the present disclosure, the following items are provided.

1. A composition for treating or preventing cancer in a subject, comprising a cell subpopulation contained in a tumor tissue infiltrating $CD106^+$ T cell population.
2. The composition according to the above item, wherein the cell subpopulation is further positive to cell markers selected from the group consisting of LAG-3, PD-1, TIM3,4-1BB, ITGAE (CD103), TIGIT, ENTPD1 (CD39), CTLA-4, and any combination thereof.
3. The composition according to any one of the above items, wherein the cell subpopulation comprises the T cells derived from the subject.
4. The composition according to any one of the above items, which is characterized by the use in combination with cancer immunotherapy.
5. The composition according to any one of the above items, wherein the cell subpopulation expresses tumor-specific TCR.
6. A composition for treating or preventing cancer in a subject, comprising the TCR expressed by the cell subpopulation contained in a tumor tissue infiltrating $CD106^+$ T cell population or the cells expressing the TCR having the same antigen specificity as the said TCR.
7. The composition according to any one of the above items, wherein the cell subpopulation is further positive to cell markers selected from the group consisting of LAG-3, PD-1, TIM3,4-1BB, ITGAE (CD103), TIGIT, ENTPD 1 (CD39), CTLA-4, and any combination thereof.
8. The composition according to any one of the above items, wherein the cells comprise the T cells derived from the subject.
9. The composition according to any one of the above items, which is characterized by the use in combination with cancer immunotherapy.
10. The composition according to any one of the above items, wherein the cells are contained in the cell subpopulation and the TCR is endogenous.
11. The composition according to any one of the above items, wherein the TCR is introduced externally into the cells.
12. The composition according to any one of the above items, wherein the cells contain artificial pluripotent stem cells (iPSC), embryonic stem cells (ES cells), T cells, or T cells differentiated from any of them.
13. The composition according to any one of the above items, further comprising a pharmaceutically acceptable carrier.
14. Use of the cell subpopulation contained in tumor tissue infiltrating $CD106^+$ T cell population in the production of pharmaceuticals for treating or preventing cancer in a subject.
15. The use according to any one of the above items, wherein the cell subpopulation is further positive to cell markers selected from the group consisting of LAG-3, PD-1, TIM3,4-1BB, ITGAE (CD103), TIGIT, ENTPD 1 (CD39), CTLA-4, and any combination thereof.
16. The use according to any one of the above items, wherein the cell subpopulation contains the T cells derived from the subject.
17. The use according to any one of the above items, characterized in that the pharmaceutical is used in combination with cancer immunotherapy.

18. The use according to any one of the above items, wherein the cell subpopulation expresses tumor-specific TCR.
19. Use of the T cell receptor (TCR) expressed by cell subpopulations contained in tumor tissue infiltrating $CD106^+$ T cell populations or the cells expressing the TCR having the same antigen specificity as it in the production of pharmaceuticals for treating or preventing cancer in a subject.
20. The use according to any one of the above items, wherein the cell subpopulation is further positive to cell markers selected from the group consisting of LAG-3, PD-1, TIM3,4-1BB, ITGAE (CD103), TIGIT, ENTPD 1 (CD39), CTLA-4, and any combination thereof.
21. The use according to any one of the above items, wherein the cells contain the T cells derived from the subject.
22. The use according to any one of the above items, characterized in that the pharmaceuticals are used in combination with cancer immunotherapy.
23. The use according to any one of the above items, wherein the cells are contained in the cell subpopulation and the TCR is endogenous.
24. The use according to any one of the above items, wherein the TCR is introduced externally into the cells.
25. The use according to any one of the above items, wherein the cells contain artificial pluripotent stem cells (iPSC), embryonic stem cells (ES cells), T cells, or T cells differentiated from any of them.
26. The use according to any one of the above items, further comprising a pharmaceutically acceptable carrier.
27. A method for treating or preventing cancer in a subject, comprising a step of administering an effective amount of a cell subpopulation contained in a tumor tissue infiltrating $CD106^+$ T cell population to the subject.
28. The method according to any one of the above items, wherein the cell subpopulation is further positive to cell markers selected from the group consisting of LAG-3, PD-1, TIM3,4-1BB, ITGAE (CD103), TIGIT, ENTPD 1 (CD39), CTLA-4, and any combination thereof
29. The method according to any one of the above items, wherein the cell subpopulation contains the T cells derived from the subject.
30. The method according to any one of the above items, characterized by being used in combination with cancer immunotherapy.
31. The method according to any one of the above items, wherein the cell subpopulation expresses tumor-specific TCR.
32. A method for treating or preventing cancer in a subject, comprising a step of administering an effective amount of the T cell receptor (TCR) expressed by cell subpopulations contained in tumor tissue infiltrating $CD106^+$ T cell populations, or an effective amount of the cells expressing the TCR having the same antigen specificity as it to the subject.
33. The method according to any one of the above items, wherein the cell subpopulation is further positive to cell markers selected from the group consisting of LAG-3, PD-1, TIM3,4-1BB, ITGAE (CD103), TIGIT, ENTPD 1 (CD39), CTLA-4, and any combination thereof
34. The method according to any one of the above items, wherein the cells contain the T cells derived from the subject.
35. The method according to any one of the above items, further comprising a step of performing cancer immunotherapy.
36. The method according to any one of the above items, wherein the cells are contained in the cell subpopulation and the TCR is endogenous.
37. The method according to any one of the above items, wherein the TCR is introduced externally into the cells.
38. The method according to any one of the above items, wherein the cells contain artificial pluripotent stem cells (iPSC), embryonic stem cells (ES cells), T cells, or T cells differentiated from any of them.
39. Cell subpopulations contained in tumor tissue infiltrating $CD106^+$ T cell populations for treating or preventing cancer in a subject.
40. The cell subpopulations according to any one of the above items, further being positive to cell markers selected from the group consisting of LAG-3, PD-1, TIM3,4-1BB, ITGAE (CD103), TIGIT, ENTPD 1 (CD39), CTLA-4, and any combination thereof.
41. The cell subpopulations according to any one of the above items, containing the T cells derived from the subject.
42. The cell subpopulations according to any one of the above items, characterized by being used in combination with cancer immunotherapy.
43. The cell subpopulations according to any one of the above items, expressing tumor-specific TCR.
44. A T cell receptor (TCR) expressed by the cell subpopulations contained in tumor tissue infiltrating $CD106^+$ T cell populations or cells expressing the TCR having the same antigen specificity as it for treating or preventing cancer in a subject.
45. The TCR or cells according to any one of the above items, wherein the cell subpopulation is further positive to cell markers selected from the group consisting of LAG-3, PD-1, TIM3,4-1BB, ITGAE (CD103), TIGIT, ENTPD 1 (CD39), CTLA-4, and any combination thereof.
46. The TCR or cells according to any one of the above items, wherein the cells contain the T cells derived from the subject.
47. The TCR or cells according to any one of the above items, characterized by being used in combination with cancer immunotherapy.
48. The TCR or cells according to any one of the above items, wherein the cells are contained in the cell subpopulation and the TCR is endogenous.
49. The TCR or cells according to any one of the above items, wherein the TCR is introduced externally into the cells.
50. The TCR or cells according to any one of the above items, wherein the cells contain artificial pluripotent stem cells (iPSC), embryonic stem cells (ES cells), T cells, or T cells differentiated from any of them.
51. A method for producing a cellular medicine for treating or preventing cancer in a subject, comprising a step of purifying $CD106^+$ T cell population from T cell population.
52. The method according to any one of the above items, further comprising a step of purifying the cell population which is positive to cell markers selected from the group consisting of LAG-3, PD-1, TIM3,4-1BB, ITGAE (CD103), TIGIT, ENTPD1 (CD39), CTLA-4, and any combination thereof.

53. The method according to any one of the above items, wherein the T cell population is isolated from the T cells which have infiltrated into tumor tissue.
54. The method according to any one of the above items, further comprising a step of providing a cellular medicine comprising the purified T cell population.
55. The method according to any one of the above items, further comprising a step of modifying the purified T cell population.
56. The method according to any one of the above items, further comprising a step of introducing the TCR possessed by the purified T cell population or the TCR having the same antigen specificity as the said TCR into cells.
57. The method according to any one of the above items, wherein the cells comprise the T cells derived from the subject.
58. The method according to any one of the above items, wherein the cells comprise artificial pluripotent stem cells (iPSC), embryonic stem cells (ES cells), T cells, or T cells differentiated from any of them.
59. A method of using the amount of the cell subpopulation contained in a CD106$^+$ T cell population of a subject as an index of responsiveness to cancer immunotherapy for the subject.
60. The method according to any one of the above items, wherein the cancer immunotherapy comprises administration of an immune checkpoint inhibitor.
61. The method according to any one of the above items, wherein the cell subpopulation is further positive to cell markers selected from the group consisting of LAG-3, PD-1, TIM3,4-1BB, ITGAE (CD103), TIGIT, ENTPD 1 (CD39), CTLA-4, and any combination thereof
62. The method according to any one of the above items, wherein the cell subpopulation is a tumor infiltration T cell subpopulation.
63. A method for diagnosing responsiveness to cancer immunotherapy for a subject, comprising a step of obtaining a CD106$^+$ T cell population from the subject, a step of determining the amount of the cell subpopulation contained in the CD106$^+$ T cell population of the subject, and a step of diagnosing responsiveness to cancer immunotherapy for the subject based on the amount of the cell subpopulation.

64. The method according to any one of the above items, wherein the cancer immunotherapy comprises administration of an immune checkpoint inhibitor.
65. The method according to any one of the above items, wherein the cell subpopulation is further positive to cell markers selected from the group consisting of LAG-3, PD-1, TIM3,4-1BB, ITGAE (CD103), TIGIT, ENTPD 1 (CD39), CTLA-4, and any combination thereof
66. The method according to any one of the above items, wherein the cell subpopulation is a tumor infiltration T cell subpopulation.
67. A method of acquiring the sequence of tumor-specific T cell receptors (TCRs), comprising a step of isolating the T cell population which is positive in CD106 expression from tumor infiltration T cells, and a step of acquiring the sequence of TCR of T cells in the T cell population.

68. The method according to any one of the above items, further comprising isolating the cell population which is further positive to cell markers selected from the group consisting of LAG-3, PD-1, TIM3,4-1BB, ITGAE (CD103), TIGIT, ENTPD1 (CD39), CTLA-4, and any combination thereof.
69. The method according to any one of the above items, wherein the step of acquiring the sequence of TCR comprises sequencing of nucleic acid sequence of the T cells.
70. The method according to any one of the above items, further comprising a step of acquiring the sequence of the TCR which have the same antigen specificity as the TCR of T cells in the T cell population.

In the present disclosure, the one or more features described above are intended to be provided in combination in addition to the explicit combination. Still further embodiments and advantages of the present disclosure are recognized by a person skilled in the art when understanding by reading the following detailed description, if necessary.

Effects of the Invention

Markers with high specificity can be provided as markers of T cells attacking tumor. Since CD106 is also a surface marker, it can be used for cell separation, and T cells that specifically attack tumors can be easily extracted. A tumor-specific cell therapy with high efficacy and few adverse effects would be possible if such T cells could be efficiently increased or T cell receptor sequences could be analyzed and produced artificially.

EMBODIMENTS FOR CARRYING OUT THE INVENTION

Figure 1:
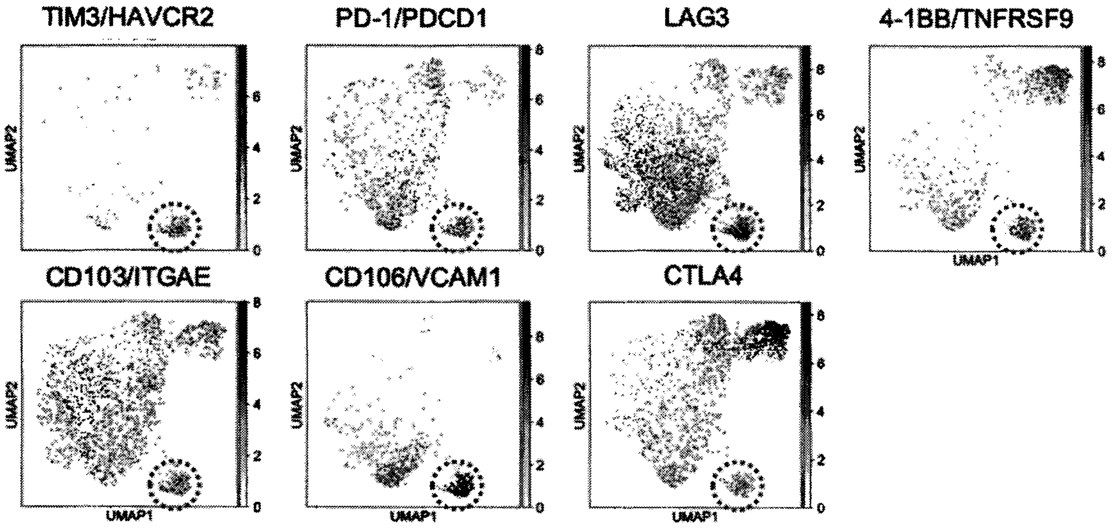
FIG. 1 shows the expression of various markers in tumor infiltrating T cells. In each panel, expression of the markers described above is shown by coloring positive cells. The cells are clustered by the expression pattern, and the areas surrounded by the circles correspond to the tumor cytotoxic T cells.

The present disclosure will be described below. It should be understood that throughout the present specification, an expression in singular form also includes its concept in plural form, unless otherwise stated. Accordingly, it should be understood that a singular article (for example, "a", "an", and "the" in English) also includes its concept in plural form, unless otherwise stated. In addition, it should also be understood that the terms used herein are used by the meanings which are commonly used in the art, unless otherwise stated. Accordingly, all technical terms and scientific terms used herein have the same meanings as those commonly understood by a person skilled in the art to which the present disclosure belongs, unless otherwise defined. In case of contradiction, the present specification (including definitions) is prioritized.

Definitions

In this specification, "about" means±10% of a subsequent numerical value, unless otherwise specified.

In this specification, "a biomarker" refers to a characteristic objectively measured and evaluated as an index of a pharmacological response to a normal biological process, a pathological process, or a therapeutic intervention.

In this specification, "cancer" refers to malignant tumor which has strong anisotropy, proliferates faster than normal cells, and may infiltrate destructively or metastasize to surrounding tissue, or a state in which such malignant tumor presents. In the present disclosure, the cancer includes solid cancer and hematopoietic tumor, but is not limited thereto.

In this specification, "cancer immunotherapy" refers to a method of treating cancer using a biological defense mechanism, such as an immune mechanism of organisms.

In this specification, "a cell subpopulation" refers to a set of arbitrary cells which have certain common characteristics in a cell population comprising cells with various properties. For those known in the art, a specific name can also be referred to as a specific cell subpopulation using such terms, and any properties (for example, expression of cell surface markers) can also be referred to as a specific cell subpopulation.

In this specification, the term "relative amount" relating to cells is used interchangeably with the "ratio". Typically, the term "relative amount" or "ratio" means the number of cells forming a desired cell subpopulation (for example, a $CD106^+$ $CD8^+$ T cell subpopulation) with respect to the number of cells forming a specific cell population (for example, a $CD8^+$ T cell population).

In this specification, "reference" refers to the amount of a marker described in this specification, or an amount to be compared for determining increase/decrease in a level. In a case of determining an amount or increase/decrease in a level before and after a certain treatment, the "reference" is for example, the amount or level before the treatment.

Fraction and Separation of Cells.

The samples for fraction and separation of cells can be appropriately collected from a subject by a conventional method. For example, it can be performed from peripheral blood, bone marrow, tumor tissue, hematopoietic tissue, spleen, normal tissue, lymph fluid, and the like of a subject. It is considered that cells that attack cancer can be obtained by isolating and if necessary, further selecting the immune cells infiltrated into tumor tissue.

Composition of immune cells in the samples of a subject can be determined by a person skilled in the art with a conventional method. Normally, for a marker defining a targeted cell subpopulation in a sample (for example, CD4), the number of positive cells can be determined by using a flow cytometry or the like. Determination of composition of cell populations is commonly performed by using a flow cytometry, however, it may also be performed by immunostaining a sample containing cells, a method using an antibody array, protein expression analysis in a sample containing cells (for example, Western blot, mass spectrometry, and HPLC, etc.), and mRNA expression analysis in a sample containing cells (for example, microarray and next generation sequencing, etc.). In order to measure the number of cells of a cell subpopulation such as a $CD106^+$ $CD8^+$ T cell subpopulation, cells other than the subpopulations of the cells may be experimentally removed from the whole cells.

Cells can be identified by examining the mRNA in each cell with gene expression analysis of a single cell to confirm the presence or absence of the mRNA encoding protein molecules of interest. Examples of the gene expression analysis of a single cell include (1) a method for performing next-generation sequencing with Quartz-Seq, (2) a method for isolating cells by using a Fluidigm C1 system or ICELL8 Single-Cell system to prepare a library with SMART-Seq v4, (3) a method for separating cells with a cell sorter, and measure by quantitative PCR using an Ambion Single Cell-to-CT kit, and (4) a CyTOF system (Helios), etc. For conformation, cells can be counted from tumor infiltration cells, and separated with a cell sorter or the like. For each separated cell, the expression level of a specific gene can be measured with a device of a quantitative PCR method by using for example, Ambion Single Cell-to-CT kit. Based on its results, it is possible to examine to which subpopulation each cell corresponds, such as $CD106^+$ $CD8^+$ T cell subpopulations, and count the number of the cells corresponding to each subpopulation.

In this specification, the fact that the expression of a certain marker is "positive" or "(marker)$^+$ cell" can be confirmed by detecting the number of one or more leads when it is confirmed by a single cell sequence, and it can be positively determined by comparing with isotype control when it is confirmed by FCM.

The Cells

In the present disclosure, a cell subpopulation having a specific marker expression pattern can be provided. In an embodiment, a cell subpopulation contained in a $CD106^+$ cell population can be provided. The cell subpopulation can be further positive to cell markers selected from the group consisting of LAG-3, PD-1, TIM3,4-1BB, TIGIT, ITGAE (CD103), ENTPD 1 (CD39), CTLA-4, and any combination thereof. In the present disclosure, the cell subpopulation described in the present disclosure can be used as cells for use in adoptive cell transfer, as cells for obtaining a tumor-specific TCR therefrom, as cells for using the level of which as an index, and/or as cells for modification. As cell populations, tumor tissue infiltrating cell populations or cell subpopulations contained therein can be used. As a surface marker of T cells that specifically attack tumor, markers such as PD-1 or 4-1BB are conventionally utilized. In addition, new attentions have been paid to CD103 and CD39 in a very recent report. In the present disclosure, from the data of single cell sequence, CD106 is considered to have the highest specificity as a surface marker, and even on the basis of a comparison in which reported markers are comprehensively viewed, it is considered to be useful in comparison with these markers.

In the present disclosure, cells or cell populations may be immune cells, precursor cells thereof. Or populations thereof. Examples of the immune cells include dendritic cells, macrophages, lymphocytes (for example, T cells (such as killer T cells, helper T cells, regulatory T cells, αβ T cells, γδ T cells, natural killer T cells), B cells, NK (natural killer) cells), neutrophils, eosinophils, basophils, and combinations thereof. In the context of treatment or prevention of cancer using cells, the cells may preferably be T cells. The cells or cell populations may contain artificial pluripotent stem cells (iPSC), embryonic stem cells (ES cells), peripheral T cells, nave T cells, memory T cells, central memory T cells (TCM), T memory stem cells (TSCM), or T cells differentiated from any of them.

The T cells in the present disclosure may be CD8-positive T cells. The cytotoxic T cell (CTL) is a type of lymphoid T cells which recognizes and destroys the cells which are foreign substances for the host (such as cancer cells). The CTL is differentiated from the T cells which express CD8 molecules on the surface.

In an embodiment of the present disclosure, a composition for treating or preventing cancer in a subject containing a cell subpopulation contained in a tumor tissue infiltrating $CD106^+$ T cell population can be provided. Alternatively, a method for treating or preventing cancer in a subject comprising a step of administering a cell subpopulation contained in a tumor tissue infiltrating CD106$^+$ T cell population can be provided.

The cell subpopulation may be further positive to the cell markers selected from the group consisting of LAG-3, PD-1, TIM3,4-1BB, TIGIT, ITGAE (CD103), ENTPD 1 (CD39), CTLA-4, and any combination thereof. The cell subpopulation may contain the T cells derived from a subject to be treated or prevented, and the T cells derived from a subject different from the subject to be treated or prevented. The cell subpopulation may express tumor-specific TCR. The cell subpopulations which express tumor-specific TCR can be identified by the markers provided in the present disclosure. In the present disclosure, the composition containing cells or adoptive cell transfer therapy may be used in combination with cancer immunotherapy.

In an embodiment of the present disclosure, the T cell receptor (TCR) expressed by cell subpopulations contained in tumor tissue infiltrating CD106$^+$ T cell populations or the cells expressing the TCRs having the same antigen specificity as it can be provided. The cells may be the cells themselves contained in tumor tissue-infiltrating CD106$^+$ T cell populations, or may be different cells expressing the TCR expressed by cell subpopulations contained in tumor tissue infiltrating CD106$^+$ T cell populations. The cells can be obtained by introduction of TCR or by screening of TCR. The cell subpopulations contained in tumor tissue infiltrating CD106$^+$ T cell populations can be further positive to the cell markers selected from the group consisting of LAG-3, PD-1, TIM3,4-1BB, TIGIT, ITGAE (CD103), ENTPD 1 (CD39), CTLA-4, and any combination thereof. The cells are contained in cell subpopulations contained in tumor tissue infiltrating CD106$^+$ T cell populations, and the TCR may be endogenous.

The TCR can be introduced externally into cells. The cells to be introduced may include for example, artificial pluripotent stem cells (iPSC), embryonic stem cells (ES cells), peripheral T cells, naive T cells, memory T cells, central memory T cells (TCM), T memory stem cells (TSCM), or T cells differentiated from any of them. The introduction of TCR can be performed by the methods described elsewhere in the present disclosure and methods known to a person skilled in the art.

A Method for Obtaining TCR

Biological defense mechanism by immune systems largely depends on specific immunity carried mainly by T cells and B cells. T cells and B cells do not respond to their own cells and molecules, and can specifically recognize and attack foreign pathogens such as virus and bacteria. For this reason, T cells and B cells have a mechanism of being able to recognize and distinguish various antigens derived from other organisms together with its own antigen by receptor molecules expressed on cell surface. In T cells, a T cell receptor (TCR) acts as an antigen receptor. Intracellular signals are transmitted by stimulation from these antigen receptors, productions of inflammatory cytokines and chemokine enhance, cell proliferation is promoted, and various immune responses are initiated.

The TCR recognizes an antigen peptide while distinguishing itself from non-self by recognizing a peptide bound to a peptide binding groove of a major histocompatibility complex (MHC) expressed on an antigen-presenting cell (peptide-MHC complex, pMHC) (Cell 1994, 76, 287-299). The TCR is a heterodimer receptor molecule consisting of two TCR polypeptide chains, where αβ-type TCR expressed by a normal T cell and γδ-type TCR having a special function are present. The α and β-chain TCR molecules form a complex with a plurality of CD3 molecules (CD3ζ chain, CD3ε chain, CD3γ chain, CD3δ chain), transmit intracellular signals after antigen recognition, and initiate various immune responses. A CD3 molecule is present in cell membrane and form a complex with a TCR, accordingly, it can be used as a marker of TCR expression. Endogenous antigens, such as viral antigens proliferated in cells accompanying viral infection and cancer antigens derived from cancer cells, are presented on MHC class I molecules as antigen peptides. In addition, antigens derived from foreign microorganisms are incorporated into antigen-presenting cells by endocytosis, and presented on MHC class II molecules after being processed. These antigens are recognized by TCR expressed by CD8$^+$ T cells or CD4$^+$ T cells, respectively. Regarding the stimulation via TCR molecules, it is also known that co-stimulation molecules such as CD28, ICOS and OX40 molecules are important.

The TCR gene consists of a large number of variable (V) region, joining (J) region, diversity (D) region, and constant (C) region, which are encoded in different regions on the genome. In the differentiation process of T cells, these gene fragments are gene-reconstructed by various combinations. The α-chain and γ-chain TCR express a gene comprising V-J-C, while the β-chain and δ-chain TCR express a gene comprising V-D-J-C. By reconstruction of these gene fragments, diversity is created. At the same time, by insertion or deletion of one or more bases occurring between V and D gene fragments or D and J gene fragments, random amino acid sequences are formed, and TCR gene sequences of higher diversity are created.

The region where a TCR molecule and the surface of pMHC complex are directly bonded (TCR footprint) consists of complementarity determining regions (CDRs) with high diversity in the V region, that is CDR1, CDR2, and CDR3 regions. Among them, the CDR3 region comprises a part of the V region, the V-D-J region formed by random sequences, and a part of the J region, and forms an antigen recognition site of the highest diversity. On the other hand, the other regions are referred to as FR (framework regions), and play a role of forming a structure as a skeleton of a TCR molecule. In the differentiation maturation process of T cells in thymus, the β-chain TCR is first genetically reconstructed and associated with a pTα molecule to form a pre-TCR complex molecule. After that, α-chain TCR is reconstructed, αβ TCR molecules are formed. At the same time, when functional αβ TCR is not formed, reconstruction occurs in the other α-chain TCR gene allele. It is known that by receiving a positive/negative selection in thymus, a TCR having an appropriate affinity is selected and acquires antigen specificity (Annual Review Immunology, 1993, 6, 309-326).

T cells produce one kind of TCR having high specificity to a specific antigen. Since a large number of antigen-specific T cells are present in a living body, a variety of TCR repertoire can be formed, and function effectively as defense mechanism against various pathogens.

In an embodiment of the present disclosure, a method for acquiring the sequence of tumor-specific T cell receptors (TCRs) can be provided. Although it is not desirable to be bound by theory, in the present disclosure, it is shown that the cell subpopulation contained in the T cell population of CD106 expression positive attacks cancer specifically, and it is believed that the tumor specific TCR can be isolated by isolating the cell subpopulation. In the present disclosure, a method for acquiring the sequence of tumor-specific T cell receptors (TCRs), comprising a step of isolating a T cell population of CD106 expression positive from tumor infiltration T cells; and a step of acquiring the sequence of the TCR of the T cells of the T cell population can be provided.

The isolation step described above may further comprise isolating a cell population that is further positive to any other marker disclosed herein (for example, a cell marker selected from the group consisting of LAG-3, PD-1, TIM3,4-1BB, TIGIT, ITGAE (CD103), ENTPD1, CTLA-4, and any combination thereof).

The acquisition of TCR sequence may comprise sequencing of nucleic acid sequences of T cells. The methods of sequencing are not limited, as long as the sequence of nucleic acid samples can be determined. Although any method known in the art can be used, it is preferable to use next-generation sequencing (NGS). Examples of the next-generation sequencing include pyrosequencing, sequencing by synthesis, sequencing by ligation, ion semiconductor sequencing, and the like, but are not limited thereto. The TCR sequence can be acquired from mRNA that does not contain introns by amplicon sequence. In addition, the TCR sequence can be acquired by sequencing the genomic sequence of T cells. Alternatively, the TCR sequence may be acquired by directly determining the amino acid sequence of TCR molecules by using mass spectrometry or Edman degradation. In the present specification, either amino acid sequence or nucleic acid sequence can be used as the "TCR sequence".

TCR Cluster

In the present disclosure, TCR having the same antigen specificity as the TCR having tumor specificity can be used. For example, TCR having the same antigen specificity as the TCR of $CD106^+$ T cell population can be used. "Having the same antigen specificity" can be determined by classifying two TCRs into the same cluster by cluster analysis as shown below. In the present disclosure, in the acquisition of tumor-specific TCR, the sequence of TCR having the same antigen specificity as the TCR of T cells of an isolated T cell population such as a $CD106^+$ T cell population can be acquired. This can be realized by subjecting one or more TCRs to cluster analysis as shown below with the TCR of T cells of an isolated T cell population. The analysis method is described in detail in publication of Japanese Patent No. 6500144, and the content of which is incorporated herein by reference.

The analysis of a TCR cluster can be performed with an analysis method comprising (i) a step of providing an amount of feature of at least two TCRs, excluding calculating an amount of feature from the three-dimensional structure model of the at least two TCRs; (ii) a step of performing machine learning of analysis of the antigen specificity or binding mode of the TCR without specifying the antigen specificity or binding mode on the basis of the amount of feature; and (iii) a step of performing classification or abnormality determination of the antigen specificity or the binding mode.

In another embodiment, a TCR cluster can be analyzed with a method comprising (a) a step of extracting an amount of feature for at least one pair of members of the TCR cluster, excluding calculating an amount of feature from the three-dimensional structure model of the at least one pair; (b) a step of calculating a distance between the antigen specificity or the binding mode for the pair by machine learning using the amount of feature, and determining whether the antigen specificity or the binding mode matches or not; (c) a step of clustering the TCR cluster on the basis of the distance; and (d) if necessary, a step of analyzing on the basis of the classification by the clustering.

In another embodiment, a TCR cluster can be analyzed with a method comprising (aa) a step of extracting an amount of feature for each of at least one pair of members of the TCR cluster, excluding calculating an amount of feature from the three-dimensional structure model of the immune entities of the sequence forming the at least one pair; (bb) a step of projecting the amount of feature into a higher-order vector space, wherein the distance on the space of the member reflects the function similarity of the member; (cc) a step of clustering the set of the immune entities based on the distance; and (dd) if necessary, a step of analyzing on the basis of the classification by the clustering.

The amount of feature may include at least one selected from the group consisting of sequence information, length of CDR1-3 sequence, sequence matching degree, sequence matching degree of framework region, total electric charge of molecules/hydrophilicity/hydrophobicity/number of aromatic amino acids, electric charge of each CDR and framework region/hydrophilicity/hydrophobicity/number of aromatic amino acids, number of each amino acid, combination of heavy chain-light chain, number of somatic mutations, position of mutation, presence of amino acid motif/matching degree, rarity with respect to reference sequence set, and odds ratio of combined HLA by reference sequence.

The calculation by machine learning can be performed by random forest or boosting with an amount of feature as an input. The clustering can be performed based on a simple threshold according to binding distance, using a hierarchical or non-hierarchical clustering method. The machine learning can be selected from the group of machine learning algorithms consisting of regression technique, neural network method, support vector machine, and random forest.

A Method for Producing the Cells

In the present disclosure, a medicine for producing the cells, in particular, the cells for use as a pharmaceutical can be provided. Although it is not desired to be bound by theory, the cells attacking tumor can be obtained by utilizing the fact that the cells contained in $CD106^+$ $CD8^+$ T cell population in tumor express tumor-specific TCR. It is considered that such cells can be used in treatment or prevention of cancer.

In an embodiment of the present disclosure, a method for producing a cellular medicine for treating or preventing cancer in a subject, comprising a step of purifying a $CD106^+$ T cell population from a T cell population can be provided. The method can further comprise a step of purifying a cell population which is positive to cell markers selected from the group consisting of LAG-3, PD-1, TIM3,4-1BB, TIGIT, ITGAE (CD103), ENTPD1, CTLA-4, and any combination thereof. The T cell population may be isolated from the T cells that have infiltrated into tumor tissue.

A cellular medicine containing the purified T cell population can be provided. The T cell populations is considered to have tumor-specific TCR and can be useful as a cellular medicine. If necessary, the purified T cell population can be cultured and/or proliferated, and provided as a pharmaceutical. The purified T cell population can be further modified, if necessary. Examples of T cell modifications include integrin $\alpha4\beta7$ and $\alpha4\beta1$ (VLA-4) interacting with CD106, and stimulation by CD3, IL-2, IL-4, and IL-7.

In some embodiments of the present disclosure, a method comprising a step of introducing the TCR that the purified T cell population has, or the TCR that has the same antigen specificity as it to cells can be provided. The acquisition and/or introduction of the TCR can be performed with the methods described elsewhere in this specification, or other methods known to a person skilled in the art. If necessary, the tumor-specific TCR may be introduced by modifying the acquired sequence. As the cells to be introduced, the T cells derived from a subject to be treated or prevented may be used, and other arbitrary immune cells may also be used. The cells to be introduced can include for example, artificial pluripotent stem cells (iPSC), embryonic stem cells (ES cells), peripheral T cells, central memory T cells (TCM), T memory stem cells (TSCM), naive T cells, memory T cells, or T cells differentiated from any of them.

The Cancer

Examples of the targeted cancer in the present disclosure include, but are not limited to, lung cancer, renal (renal cell) cancer, prostate cancer, gastric cancer, testis cancer, hepatocyte cancer, skin cancer, esophageal cancer, melanoma, pancreatic cancer, pancreas cancer, bone tumor, osteosarcoma, colon cancer, bone soft part tumor, biliary tract cancer, multiple myeloma, malignant lymphoma (Hodgkin's lymphoma, non-Hodgkin's lymphoma), urinary tract cancer, uterine cancer (body and neck), head neck cancer, brain tumor, thymus tumor, thyroid cancer, mesothelioma, anal cancer, penis cancer, primary unknown cancer, ovarian cancer, breast cancer, and the like.

Cancer Immunotherapy

In the present specification, a "cancer immunotherapy" refers to a method of treating cancer using an immune function of organisms. Cancer immunotherapies includes those increasing immune function against cancer, and those inhibiting immune avoidance function of cancer. Furthermore, cancer immunotherapies include active immunotherapy which activates in vivo immune function, and passive immunotherapy which activates an immune function in vitro or returns proliferated immune cells back into the body. Examples of a cancer immunotherapy include a non-specific immune-activator, cytokine therapy, cancer vaccine therapy, dendritic cell therapy, adoptive immunotherapy, non-specific lymphocyte therapy, cancer antigen-specific T cell therapy, antibody therapy, immune checkpoint inhibition therapy, and CAR-T therapy, etc. In the present disclosure, a method which uses the amount of cell subpopulations that specifically attack tumor as an index of responsiveness to cancer immunotherapy for a subject can be provided.

In an embodiment, a method which uses the amount of cell subpopulations contained in a $CD106^+$ T cell population of a subject as an index of responsiveness to cancer immunotherapy for a subject can be provided. The cancer immunotherapy may comprise the administration of an immune checkpoint inhibitor. As the cell subpopulations, those which are further positive to cell markers selected from the group consisting of LAG-3, PD-1, TIM3,4-1BB, TIGIT, ITGAE (CD103), ENTPD1, CTLA-4, and any combination thereof can be used. The amount of cell subpopulations in any part of the body can be used, however, the amount of cell subpopulations in tumor infiltration T cells is preferably used.

In recent years, much attention has been paid to immune checkpoint (inhibition) therapy using an immune checkpoint inhibitor (Pardoll D M. The blockade of immune checkpoints in cancer immunotherapy. Nat Rev Cancer. 2012 Mar. 22; 12(4):252-64). Cancer cells express various proteins on their surfaces, which leads to avoidance of attack by immune cells such as T cells. Therefore, it is considered that in a normal state, cancer tissue cannot be removed only by the immune function of a living body. The immune checkpoint inhibitor can remove cancer efficiently by the immune function of the living body by inhibiting the ligand-receptor interaction or the like in charge of the transmission of the inhibitory signal from the cancer tissue to the immune function. An embodiment of the present disclosure is a method which uses the amount of subpopulation contained in a $CD106^+$ T cell population as an index for predicting the responsiveness of a subject to an immune checkpoint inhibitor as described below. Another embodiment of the present disclosure is a method of administering an immune checkpoint inhibitor as shown below to a subject which is selected based on the amount of cell subpopulation contained in a $CD106^+$ T cell population. In another embodiment, a method for interrupting or stopping or avoiding an immune checkpoint inhibitor to a subject that has been found to have no responsiveness based on the amount of cell subpopulation contained in a $CD106^+$ T cell population is provided.

A typical example of immune checkpoint inhibitor is PD-1 inhibitor. Examples of PD-1 inhibitor include, but are not limited to, nivolumab (sold as Opdivo™) and pembrolizumab (sold as Keytruda™), which are anti-PD-1 antibodies. The anti-PD-1 antibody is considered to exhibit an anti-cancer effect by releasing the inhibition of T cell activation by PD-1 signal. It is considered that when PD-1 (programmed death 1) interacts with PD-L1 or PD-L2, SHP-2, a kind of tyrosine decarboxylase, is recruited to the cytoplasmic domain of PD-1, and ZAP70, a T cell receptor signaling protein, is inactivated, whereby the activation of T cells is suppressed (Okazaki, T., Chikuma, S., Iwai, Y. et al.: A rheostat for immune responses: the unique properties of PD-1 and their advantages for clinical application. Nat. Immunol., 14, 1212-1218 (2013)). Besides, PD-L1 is also considered to interact with CD80 and suppress T cell activation (Butte, M. J., Keir, M. E., Phamduy, T. B. et al.: PD-L1 interacts specifically with B7-1 to inhibit T cell proliferation. Immunity, 27, 111-122 (2007)). It is considered that PD-1 is highly expressed in killer T cells and natural killer cells which are infiltrating into cancer tissue, and the immune response is attenuated by PD-L1 on tumor. When the attenuation of the immune response by the PD-1 signal is inhibited by the anti-PD-1 antibody, the effect of enhancing antitumor immune response can be achieved.

Other examples of immune checkpoint inhibitor include PD-L1 inhibitors (for example, an anti-PD-L1 antibody such as avelumab, durvalumab, or atezolizumab). The PD-L1 inhibitor inhibits PD-1 pathway by binding it at PD-L1 side and produces anti-tumor immune response.

Other examples of immune checkpoint inhibitor include CTLA-4 inhibitors (for example, an anti-CTLA-4 antibody such as ipilimumab or tremelimumab). The CTLA-4 inhibitor activates T cells in a path different from PD-1 inhibition, and produces anti-tumor immune response. T cells are activated by the interaction of CD28 on the surface with CD80 or CD86. However, even in the case of T cells activated once, CTLA-4 (cytotoxic T-lymphocyte-associated antigen 4) expressed on the surface is considered to interact preferentially with CD80 or CD86 with higher affinity than CD20, thereby suppressing the activation. The CTLA-4 inhibitor produces anti-tumor immune response by preventing the inhibition of the interactions between CD20 and CD80 or CD86 by inhibiting CTLA-4.

In a further embodiment, the immune checkpoint inhibitor may target an immune checkpoint protein such as TIM-3, LAG-3, B7-H3, B7-H4, B7-H5 (VISTA), or TIGIT, etc.

Although the immune checkpoint as described above is considered to suppress an immune response to its own tissue, the immune checkpoint increases in T cells even when an antigen such as virus is present in a living body for a long period of time. Regarding tumor tissue, antigens present in a living body for a long period of time. Therefore, it is considered that anti-tumor immune is avoided by these immune checkpoints. The immune checkpoint inhibitor described above invalidates such an avoidance function, and exhibits anti-tumor effects.

In an embodiment of the present disclosure, an index for predicting the responsiveness to cancer immunotherapy for a subject with cancer is provided. The response to cancer immunotherapy can be determined based on RECIST v1.1 (New response evaluation criteria in solid tumors: Revised RECIST guideline (version 1.1)).

The effect of cancer treatment can be determined according to the changes in tumor size, etc. as complete response (CR), partial response (PR), progressive disease (PD), or stable disease (SD).

In the present specification, the term "responder" refers to a subject which exhibits complete response or partial response to cancer therapy. In the present specification, the term "non-responder" refers to a subject which exhibits progressive disease or stable disease to cancer therapy.

The responsiveness to cancer therapy of a subject includes the situations that a subject is a "responder" and that a subject is a "non-responder". Therefore, the determination of the responsiveness to cancer therapy of a subject includes the determination of whether a subject is a responder or a non-responder.

In an aspect of the present disclosure, whether a subject is a "responder" or a "non-responder" is predicted or determined according to the amount of cell subpopulations contained in $CD106^+$ T cell population. Regarding the timing of the determination, although the prediction is preferably carried out before a therapy is started, the determination may be carried out after a therapy is started. This is because it is also possible to determine whether the currently performing treatment is appropriate or not. Alternatively, the prognosis can also be determined using the amount of cell subpopulation included in $CD106^+$ T cell population of the present disclosure. For example, the amount of cell subpopulations contained in $CD106^+$ T cell population of the present disclosure can be used to predict that a responder might become a non-responder, that is, recurrence. Further, regarding the timing of determination, it is possible to determine the prognosis by analyzing the composition of cell subpopulations over time after cancer immunotherapy has been applied (for example, after the administration of an immune checkpoint inhibitor).

Companion Application of Immune Checkpoint Inhibitors

In a further aspect of the present disclosure, the present disclosure can provide a composition containing an immune checkpoint inhibitor for treating cancer in a subject with a large amount of cell subpopulation contained in a $CD106^+$ T cell population. The administration of such immune checkpoint inhibitor to a subject with a large amount of cell subpopulation contained in a $CD106^+$ T cell population may be advantageous, because it is considered that there are many cells that attack tumor. Besides, a subject with a less amount of cell subpopulation contained in a $CD106^+$ T cell population can be determined as a non-responder, and it is also possible to determine that an immune checkpoint inhibitor is not administered or the administration is interrupted or stopped.

The composition of the present disclosure is preferably a pharmaceutical composition. Examples of the immune checkpoint inhibitor contained as an active ingredient thereof include a PD-1 inhibitor. Examples of the PD-1 inhibitor include nivolumab and pembrolizumab, which are anti-PD-1 antibodies. The composition can be formulated in any dosage form, such as aerosol, liquid agent, extract, elixir, capsule, granule, pill, ointment, powder, tablet, solution, suspension, and emulsion, etc. The compositions may comprise any pharmaceutically acceptable additive and/or excipient known in the art. The compositions of the present disclosure can be administered by any appropriate route determined by a person skilled in the art, including, but are not limited to, intravenous, infusion, oral, parenteral, transdermal, and the like.

The Compositions

In the present disclosure, the compositions containing immune checkpoint inhibitors or cells may be used in combination with other cancer treatments. Examples of the other cancer treatments include, but are not limited to, other cancer immunotherapy, radiotherapy, chemotherapy, thermotherapy, and surgical procedures, etc. The compositions containing immune checkpoint inhibitors or cells may be administered in combination with one or more additional agents. The one or more additional agents may be any chemotherapeutic agents, or may contain a second immune checkpoint inhibitor.

In an embodiment of the present disclosure, a composition containing an immune checkpoint inhibitor is provided. The composition containing an immune checkpoint inhibitor of the present disclosure is typically administered systemically or locally in an oral or parenteral form. The composition containing an immune checkpoint inhibitor of the present disclosure is considered to be able to exhibit a remarkable therapeutic effect by being administered to a subject which is shown to have a large number of cells attacking tumor by the method described in this specification.

The dose varies depending on age, body weight, symptom, therapeutic effect, administration method, treatment time, etc. Normally, for example, it is administered orally from 0.1 mg to 100 mg once per adult and once to several times per day, or administered parenterally (preferably intravenously administered) from 0.01 mg to 30 mg once per adult and once to several times per day, or administered intravenously by continuous infusion for 1 hour to 24 hours per day. It is obvious that the dose varies depending on various conditions, so that a less amount than the above-mentioned dose may be sufficient, or an amount exceeding the above-mentioned range may be necessary.

The composition containing an immune checkpoint inhibitor or the composition containing cells may be in a dosage form of oral solid agent or oral liquid agent for oral administration, or injection agent, external preparation, or suppository, etc. for parenteral administration. The oral solid agent for oral administration includes tablet, pill, capsule, powder, and granule, etc. The capsule includes hard capsule and soft capsule.

If necessary, the composition of the present disclosure may have one or more active ingredients (for example, cells or antibodies against immune checkpoint protein) as they are, or be mixed with an excipient (such as lactose, mannitol, glucose, microcrystalline cellulose, and starch, etc.), a binder (such as hydroxypropyl cellulose, polyvinylpyrrolidone, and magnesium metasilicate aluminate, etc.), a disintegrant (such as fibrinous glycolic acid calcium, etc.), a lubricant (such as magnesium stearate, etc.), a stabilizer, and a dissolution aid (such as glutamic acid and aspartic acid, etc.), etc. and formulated according to a conventional method for use. In addition, if necessary, it may be coated with a coating agent (such as white sugar, gelatin, hydroxypropyl cellulose, and hydroxypropylmethyl cellulose phthalate, etc.), and may be coated with two or more layers. Further, a capsule of a substance capable of being absorbed, such as gelatin, is also included.

An injection agent for parenteral administration includes a solid injection agent that is used by dissolving or suspending in a solution, a suspension, an emulsion, or a solvent for use. The injection agent is used by dissolving, suspending or emulsifying one or more active substances in a solvent. As the solvent, for example, distilled water for injection, physiological saline, vegetable oil, and alcohols such as propylene glycol, polyethylene glycol, and ethanol are used. Furthermore, the injection agent may contain a stabilizer, a dissolution aid (glutamic acid, aspartic acid, polysorbate 80®, etc.), a suspension agent, an emulsifier, an analgesic agent, a buffer agent, a preservative, or the like. These are prepared with sterilization or sterile procedures in the final process. In addition, regarding a sterile solid agent, for example, a freeze-dried product can be produced, and dissolved in sterile distilled water for injection or other solvents before use.

The reference documents such as scientific documents, patents, and patent applications, etc. cited in this specification are incorporated herein by reference herein each to the same extent as described in detail.

The present disclosure has been described above with reference to preferred embodiments for easy understanding. Hereinafter, the present disclosure will be described based on examples. However, the above descriptions and the following examples are provided only for the purposes of illustration, but not for the purposes of limiting the present disclosure. Therefore, the scope of the present disclosure is not limited to the embodiments or examples described specifically herein, but is only limited to the scope of claims.

EXAMPLES

Example 1: Specificity to Tumor Cytotoxic T Cells Expressing CD10 Materials and Methods Tumor tissue was obtained from a surgical specimen of a patient with melanoma remarkably effective with anti-PD-1 antibody before the start of treatment with anti-PD-1 antibody. The tumor tissue was subjected to enzymatic treatment by adding collagenase and DNase and stirring at 37° C. for 30 minutes, and cells were separated. From the cell mixture of the cells of the tumor tissue and tumor infiltration immune cells, CD3-positive cells were sorted by using BD FACSAria III, and T cells expressing TCR were obtained.

For each of the obtained T cells, the gene expression of the marker candidate and the TCR sequence were determined by sequencing using the 5 Prime Kit and V (D) J Enrichment Kit of 10× Chronium. HISEQ3000 was used as the sequencer.

An UMAP plot was produced by using the obtained fastq file with the UMAP library of Python. The expression of each gene was mapped onto the obtained UMAP plot.

Results

The results are shown in FIG. 1. In each panel of FIG. 1, the cells expressing the marker described positively is indicated by coloring. The cells are clustered according to their expression pattern, and the areas surrounded by circles correspond to tumor cytotoxic T cells. It is understood that the CD106 (VCAM 1)-positive cells are expressed with high specificity to the tumor cytotoxic T cells population. CD106 can be used as a selective marker of tumor cytotoxic T cells having specificity higher than that of other surface markers. The TCR sequence can be acquired with its β-chain from 90% or more of the cells, and its α-chain from 60% to 90% of the cells.

Example 2: Tumor Attack of CD106-Positive Cell Population Materials and Methods In the same manner as in Example 1, the cells of tumor tissue were separated. The CD3-positive cells were sorted from the mixture using BD FACSAria III, and the T cells expressing TCR were obtained as tumor infiltration T cells. The tumor infiltration T cells were co-cultured with cell lines established from self-tumor, and the secretion of IFNγ was compared with the case without stimulation. The secretion of IFNγ was determined by intracellular staining with anti-IFNγ antibodies. The cell staining was carried out with anti-PD-1 antibody, anti-TIGIT antibody, anti-LAG3 antibody, and anti-CD106 antibody. As negative control, isotype control antibody for anti-CD106 antibody was used.

Results

Figure 2:
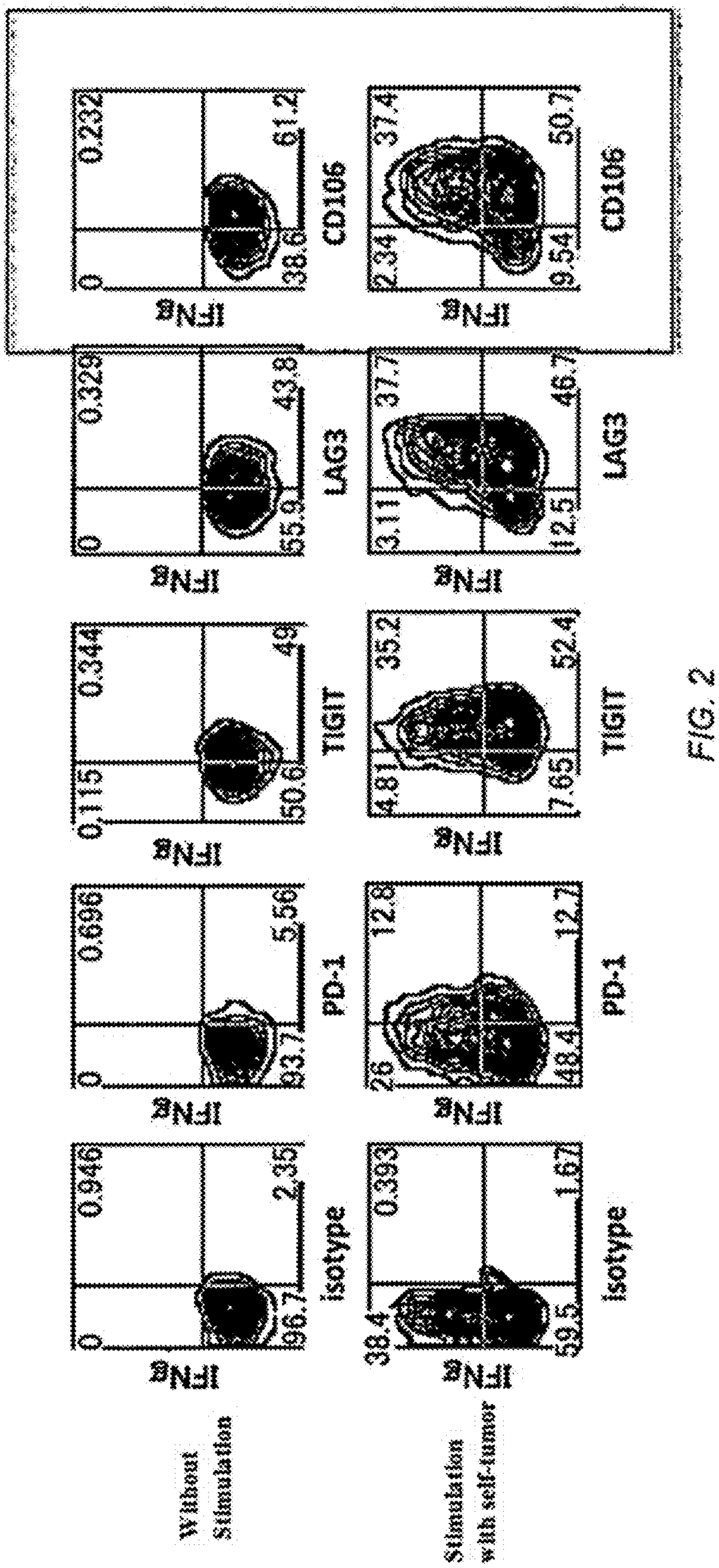
FIG. 2 shows the secretion of IFNγ when self-tumor stimulation is performed in a cell subpopulation sorted by marker expression. From the fact that in the positive fraction of the CD106 IFNγ appeared by stimulation, and in the positive fraction of other markers IFNγ appeared by stimulation, while in the negative fraction of other markers IFNγ also appeared, it can be understood that the degree of specificity of the other markers is inferior to CD106.

The results are shown in FIG. 2. From the fact that in the positive fraction of the CD106 IFNγ appeared by stimulation, and in the positive fraction of other markers IFNγ appeared by stimulation, while in the negative fraction of other markers IFNγ also appeared, it can be understood that the degree of specificity of the other markers is inferior to CD106.

Example 3: Production of the Cells

Tumor tissue of a patient was obtained, and the cells were separated by enzymatic treatment. Tumor infiltrating T cells were isolated as a CD3-positive fraction with a flow cytometry. From the CD3-positive fraction, a fraction which was both CD106-positive and CD8-positive was further isolated.

The cells of the isolated fraction were cultured and proliferated, and used as acellular medicine.

The nucleic acid sequence of the cells of the isolated fraction was determined, and the TCR sequence was acquired. A vector having the acquired TCR sequence was designed and introduced into other cells. The introduced cells were cultured and proliferated, if necessary, and used as acellular medicine.

Example 4: Prediction of the Effect of Cancer Immunotherapy

Information about tumor infiltration T cells of a patient subjected to cancer immunotherapy was acquired.

The amounts of cell subpopulations contained in $CD106^+$ T cell population in tumor infiltrating T cells ($CD106^+$ T cell subpopulation, $CD106^+$ $CD8^+$ T cell subpopulation, LAG-$3^+$ $CD106^+$ $CD8^+$ T cell subpopulation, PD-$1^+$ $CD106^+$ $CD8^+$ T cell subpopulation, $TIM3^+$ $CD106^+$ $CD8^+$ T cell subpopulations, 4-$1BB^+$ $CD106^+$ $CD8^+$ T cell subpopulation, $TIGIT^+$ $CD106^+$ $CD8^+$ T cell subpopulation, $ITGAE^+$ $CD106^+$ $CD8^+$ T cell subpopulation, $ENTPD1^+$ $CD106^+$ $CD8^+$ T cell subpopulation, and CTLA-$4^+$ $CD106^+$ $CD8^+$ T cell subpopulation) were acquired.

By comparing the therapeutic effect (CR, PR, SD, PD) with the amounts of cell subpopulations of a patient subjected to cancer immunotherapy, it is verified that the amount of a specific cell subpopulation can be an index.

Note

As described above, the present disclosure has been exemplified by using the preferred embodiments of the present disclosure. However, it is understood that the scope of the present disclosure should be interpreted only by the scope of the claims. It is understood that the contents of the patents, patent applications and other documents cited herein are to be incorporated herein by reference to this specification in the same manner as described herein. The present application is accompanied by the priority claim to the Japanese patent application No. 2019-128517 filed on Jul. 10, 2019, and all contents of the application are incorporated by reference in the present application.

INDUSTRIAL APPLICABILITY

The present disclosure can be used in medical, pharmaceutical, healthcare, biological, biochemical fields, etc.

The invention claimed is:

1. A composition for treating or preventing cancer in a subject, comprising isolated $CD106^+$ T cells, a subpopulation of isolated infiltrating cells contained in a tumor tissue and a pharmaceutically acceptable additive and/or excipient and an immune checkpoint inhibitor, wherein the $CD106^+$ T cells are $CD106^+$ $CD8^+$ T cells, LAG-$3^+$ $CD106^+$ $CD8^+$ T cells, PD-$1^+$ $CD106^+$ $CD8^+$ T cells, $TIM3^+$ $CD106^+$ $CD8^+$ T cells, 4-1BB+$CD106^+$ $CD8^+$ T cells, TIGIT+$CD106^+$ $CD8^+$ T cells, $ITGAE^+$ $CD106^+$ $CD8^+$ T cells, $ENTPD1^+$ $CD106^+$ $CD8^+$ T cells, CTLA-$4^+$ $CD106^+$ $CD8^+$ T cells, or any combination thereof.

2. The composition according to claim 1, wherein the cell subpopulation expresses tumor-specific TCR.

3. The composition according to claim 2, wherein the TCR is endogenous.

4. The composition according to claim 1, wherein the cells comprise artificial pluripotent stem cells (iPSC), embryonic stem cells (ES cells), T cells, or T cells differentiated from any of them.

5. The composition of claim 1, wherein the immune checkpoint inhibitor is selected from the group consisting of a PD-1 inhibitor, a PD-L1 inhibitor, a CTLA-4 inhibitor and any combination thereof.

* * * * *